(12) United States Patent
Al-Tawfiq et al.

(10) Patent No.: US 12,061,182 B2
(45) Date of Patent: Aug. 13, 2024

(54) ION CONDUCTIVITY FILTER AND MEASUREMENT SYSTEM

(71) Applicant: Saudi Arabian Oil Company, Dhahran (SA)

(72) Inventors: Ali M. Al-Tawfiq, Qatif (SA); Ali M. Al-Sulaiman, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 147 days.

(21) Appl. No.: 16/942,589

(22) Filed: Jul. 29, 2020

(65) Prior Publication Data

US 2022/0034860 A1 Feb. 3, 2022

(51) Int. Cl.
*G01N 33/18* (2006.01)
*G01N 27/333* (2006.01)

(52) U.S. Cl.
CPC ....... *G01N 33/1813* (2013.01); *G01N 27/333* (2013.01)

(58) Field of Classification Search
CPC .................. G01N 33/1813; G01N 27/333
See application file for complete search history.

(56) References Cited

U.S. PATENT DOCUMENTS

| | | | |
|---|---|---|---|
| 4,713,772 A | 12/1987 | Carlson et al. | |
| 4,766,550 A | 8/1988 | Byers et al. | |
| 6,017,445 A * | 1/2000 | Lok | B01D 61/44 |
| | | | 210/85 |
| 6,114,176 A * | 9/2000 | Edgson | C12Q 1/58 |
| | | | 435/12 |
| 6,936,156 B2 * | 8/2005 | Smith | G01N 33/18 |
| | | | 205/789 |
| 8,562,803 B2 | 10/2013 | Nyberg et al. | |
| 8,678,080 B2 | 3/2014 | Curole et al. | |
| 2005/0274676 A1 | 12/2005 | Kumar et al. | |

(Continued)

FOREIGN PATENT DOCUMENTS

CN 108726740 A * 11/2018
CN 210419536 U * 4/2020

(Continued)

OTHER PUBLICATIONS

Arai et al., Translation of JP-2010029104-A, 2010 (Year: 2010).*

(Continued)

*Primary Examiner* — Luan V Van
*Assistant Examiner* — Shizhi Qian
(74) *Attorney, Agent, or Firm* — Fish & Richardson P.C.

(57) ABSTRACT

An apparatus for measuring the cation conductivity of a fluid sample includes a housing having an inlet disposed at a first end of the housing and an outlet disposed at a second end of the housing, the second end opposite the first end, wherein the inlet of the housing is configured to receive the fluid sample. The apparatus includes a first cellulose filter disposed in the housing adjacent to the inlet; a second cellulose filter disposed in the housing adjacent to the outlet; and a cation exchange resin filter disposed in the housing between the first cellulose filter and the second cellulose filter. The outlet of the housing is configured to be fluidically connected to a cation conductivity sensor configured to measure a cation conductivity of an effluent output from the outlet of the housing.

10 Claims, 4 Drawing Sheets

(56) References Cited

U.S. PATENT DOCUMENTS

| | | | | |
|---|---|---|---|---|
| 2008/0302651 | A1* | 12/2008 | Arai | C02F 1/4602 |
| | | | | 204/157.15 |
| 2013/0255955 | A1* | 10/2013 | Curole | E21B 43/24 |
| | | | | 166/52 |
| 2014/0190876 | A1* | 7/2014 | Meyer | A61M 1/3472 |
| | | | | 210/85 |
| 2014/0196753 | A1* | 7/2014 | Jessen | B01J 49/53 |
| | | | | 134/109 |
| 2017/0320909 | A1 | 11/2017 | Xenopoulos et al. | |

FOREIGN PATENT DOCUMENTS

| | | |
|---|---|---|
| EP | 2816348 | 12/2014 |
| JP | S6091259 | 5/1985 |
| JP | S60152931 | 8/1985 |
| JP | 2004515351 | 5/2004 |
| JP | 2007183133 | 7/2007 |
| JP | 2010029104 | 2/2010 |
| JP | 2010029104 A * | 2/2010 |

OTHER PUBLICATIONS

Li et al., Translation of CN 210419536U, 2014 (Year: 2014).*
Dai et al., English translation of CN108726740A, 2018 (Year: 2018).*
PCT International Search Report and Written Opinion in International Appln. No. PCT/US2021/043652, dated Nov. 5, 2021, 16 pages.
Carvalho et al., Cation conductivity and power plant reliability: A 20-plant survey, Power Plant Chemistry; 4(5), May 2002, 6 pages.
Carvalho et al., "Is cation conductivity monitoring relevant for today's combined cycle power plant? Yet another case study says it is not," PowerPlant Chemistry, 2007, 5 pages.
Cashin et al., "Benefit from monitoring degassed cation conductivity of condensate," Power, 1987, 39-41, 3 pages.

* cited by examiner

ION CONDUCTIVITY FILTER AND MEASUREMENT SYSTEM

BACKGROUND

Cation conductivity is a test that can be used to monitor water purity. For instance, cation conductivity is used for monitoring of the presence of contaminants in steam generation systems, such as in a heat recovery steam generator (HRSG). HRSG systems are treated with chemicals such as ammonia or hydrazine. Cation conductivity can be used to detect contamination of an HRSG system by cooling water, such as sea water or well water as cooling water, by monitoring for the presence of salts, such as sodium chloride.

SUMMARY

In an aspect, an apparatus for measuring the cation conductivity of a fluid sample includes a housing having an inlet disposed at a first end of the housing and an outlet disposed at a second end of the housing, the second end opposite the first end, wherein the inlet of the housing is configured to receive the fluid sample. The apparatus includes a first cellulose filter disposed in the housing adjacent to the inlet; a second cellulose filter disposed in the housing adjacent to the outlet; and a cation exchange resin filter disposed in the housing between the first cellulose filter and the second cellulose filter. The outlet of the housing is configured to be fluidically connected to a cation conductivity sensor configured to measure a cation conductivity of an effluent output from the outlet of the housing.

Embodiments may include one or any combination of two or more of the following features.

The first cellulose filter includes a 0.45 µm cellulose filter.

The second cellulose filter includes a 0.45 µm cellulose filter.

The cation exchange resin filter is formed of a material including acidic functional groups.

The apparatus includes a side inlet disposed along a length of the housing; and a side outlet disposed along the length of the housing. The side inlet and side outlet are aligned with the cation exchange resin filter. The side inlet is configured to be fluidically connected to a fluid source. The apparatus includes a source of regeneration fluid fluidically connected to the side inlet. The source of regeneration fluid includes a source of hydrochloric acid or sulfuric acid. A distance between the side inlet and the inlet of the housing is less than a distance between the side outlet and the inlet of the housing.

The apparatus includes the cation conductivity sensor.

In an aspect, a method of measuring the cation conductivity of a fluid sample includes flowing the fluid sample through an ion conductivity filter, including flowing the fluid sample across a first cellulose filter disposed in a housing, wherein the first cellulose filter is disposed adjacent to an inlet to the ion conductivity filter, the inlet disposed at a first end of the housing; flowing the fluid sample from the first cellulose filter across a cation exchange resin filter disposed in the housing; and flowing the fluid sample from the cation exchange resin filter across a second cellulose filter disposed in the housing. The second cellulose filter is disposed adjacent to an outlet from the ion conductivity filter, the outlet disposed at a second end of the housing, the second end opposite the first end. The method includes providing an effluent from the outlet of the ion conductivity filter to a cation conductivity sensor configured to measure a cation conductivity of the effluent.

Embodiments can include one or any combination of two or more of the following features.

The method includes by the cation conductivity sensor, measuring the cation conductivity of the effluent. The method includes comparing the measured cation conductivity of the effluent to a baseline cation conductivity. The method includes determining a contamination of the fluid sample based on the measured cation conductivity of the effluent. The method includes determining that the fluid sample is contaminated when the measured cation conductivity of the effluent exceeds a baseline cation conductivity by at least a threshold amount.

Flowing the fluid sample across the cation exchange resin filter includes binding contaminant cations from the fluid sample to the cation exchange resin filter. The cation exchange resin filter releases hydrogen ions responsive to the binding of contaminant cations.

Flowing the fluid sample across the first cellulose filter includes removing suspended solids from the fluid sample.

Flowing the fluid sample across the second cellulose filter includes removing particulate matter from the cation exchange resin filter from the fluid sample.

The method includes flowing a regeneration fluid across the cation exchange resin filter. The method includes flowing the regeneration fluid into a side inlet disposed along a length of the housing and aligned with the cation exchange resin filter, across the cation exchange resin filter, and out a side outlet disposed along the length of the housing and aligned with the cation exchange resin filter.

The method includes rinsing the cation exchange resin filter with a cleaning fluid. The method includes flowing the cleaning fluid into a side inlet disposed along a length of the housing and aligned with the cation exchange resin filter, across the cation exchange resin filter, and out a side outlet disposed along the length of the housing and aligned with the cation exchange resin filter.

The method includes detaching the ion conductivity filter from the cation conductivity sensor. The method includes filling the housing with a fluid and capping the inlet and outlet of the ion conductivity filter. The method includes storing the capped, detached ion conductivity filter.

In an aspect, a method of making an apparatus for measuring the cation conductivity of a fluid sample includes disposing a first cellulose filter in the interior of a housing adjacent to an inlet disposed at a first end of the housing; disposing a cation exchange resin filter in the interior of the housing adjacent to the first cellulose filter; and disposing a second cellulose filter in the interior of the housing adjacent to the cation exchange resin filter and adjacent to an outlet disposed at a second end of the housing, the second end opposite the first end. The outlet is configured to be fluidically connected to a cation conductivity sensor configured to measure a cation conductivity of an effluent output from the outlet.

The approaches described here can have one or more of the following advantages. The laboratory-scale ion conductivity measurement system described here are small, portable, and inexpensive to install and maintain. These systems provide a low-cost approach to determining contamination of fluid samples in a laboratory setting.

The details of one or more implementations are set forth in the accompanying drawings and the description below. Other features and advantages will be apparent from the description and drawings, and from the claims.

DETAILED DESCRIPTION

We describe here a laboratory-scale ion conductivity measurement system, such as a cation conductivity measurement system. The ion conductivity measurement system includes an ion conductivity filter that includes three filters disposed in a housing: a first cellulose filter for removal of solids suspended in a fluid sample, an ion exchange resin filter for ion exchange with contaminant ions in the fluid sample, and a second cellulose filter for removal of particulate matter from the ion exchange resin filter. The ion conductivity (for instance, the cation conductivity) of the effluent exiting the ion conductivity filter is measured to characterize the purity of the fluid sample.

Figure 1:
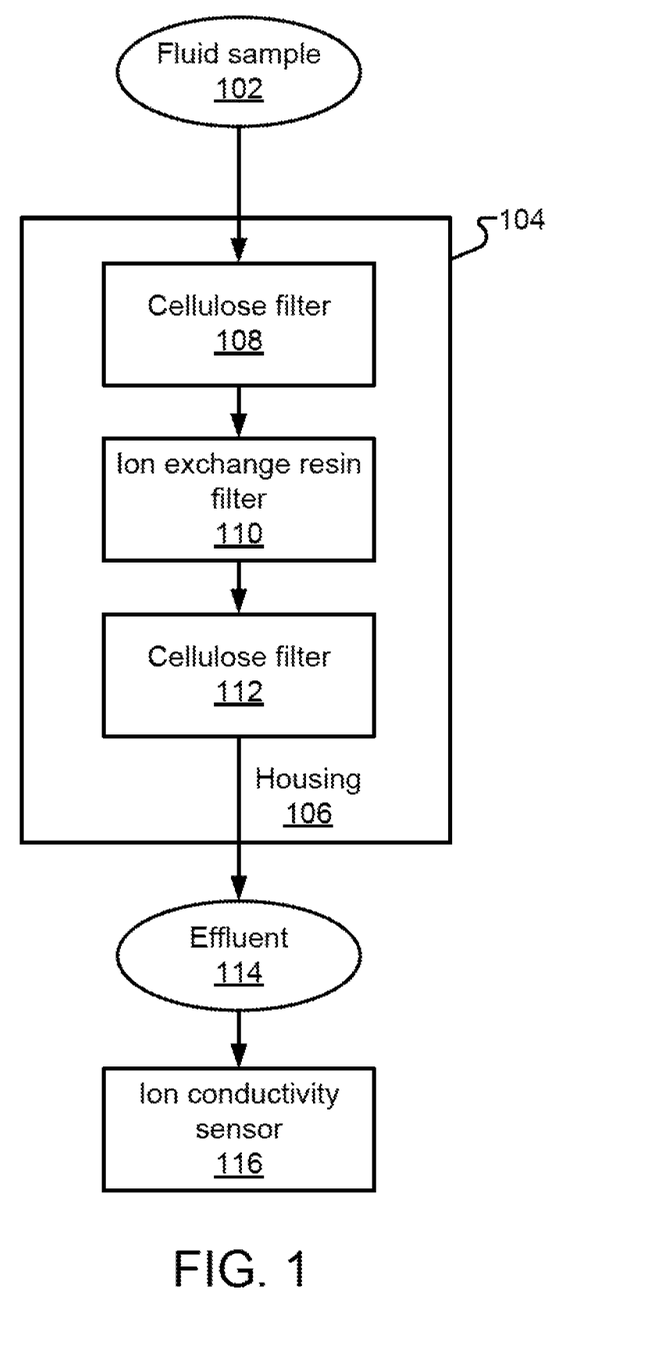
FIG. 1 is a diagram of an electrical conductivity measurement system.

Referring to FIG. 1, a laboratory-scale ion conductivity measurement system 100 is configured for measurement of the ion conductivity (for instance, the cation conductivity) of a fluid sample 102. The fluid sample can be, for instance, a fluid sample from a steam generation facility, such as a power plant. For instance, the fluid sample can be steam, condensate, feed water, boiler water, evaporator water, or other fluid sample from a power plant. In an example, the fluid sample can be fluid obtained from a steam generation system, such as a heat recovery steam generator (HRSG). Measurement of the ion conductivity of the fluid sample can provide an indication of the purity of the fluid sample and hence the purity of the steam or water. Fluid purity in a power plant is important, for instance, to avoid the danger of corrosion of power plant elements or deposition of contaminants from the fluid onto power plant elements.

Fluid in a power plant is sometimes treated with treatment chemicals such as ammonia or hydrazine, for instance, to reduce the potential for corrosion. In addition, power plants are sometimes cooled with cooling fluid such as sea water or well water, which include salts such as sodium chloride. Contamination of the power plant fluid by cooling water will result in an increase in the salt concentration in the power plant fluid, which can be detected by ion conductivity measurements. With the laboratory-scale ion conductivity measurement system 100, salt contamination can be detected in small samples of fluid. By detecting salt contamination on a small scale, the need for an online ion conductivity analyzer integrated into the power plant can be reduced, reducing the capital and maintenance costs and space requirements associated such online analyzers.

The fluid sample 102 is provided to an ion conductivity filter 104 in the ion conductivity measurement system 100. The ion conductivity filter 104 includes multiple filter components disposed in a housing 106, such as three layers of filters. The filter components include a first cellulose filter 108 that is configured to filter solids suspended in the fluid sample 102. The filter components include an ion exchange resin filter 110 that acts as a medium for ion exchange, such as cation or anion exchange. The filter components also include a second cellulose filter 112 that is configured to filter particulate matter from the ion exchange resin filter 110. Filtered effluent 114 exiting the ion conductivity filter 104 flows to an ion conductivity sensor 116 that measures the ion conductivity (such as the cation or anion conductivity) of the effluent 114. The ion conductivity of the effluent is an indication of the level of contamination of the fluid sample, as discussed infra.

The ion exchange resin filter 110 is formed of a material that is capable of binding to dissolved ions in the fluid sample 102. For instance, to facilitate detection of contaminant salts in the fluid sample, the ion exchange resin filter 110 can be a cation exchange filter that is formed of a material that is capable of binding to cations in the fluid sample 102. As the fluid sample 102 flows across the cation exchange resin filter, dissolved cations from the contaminant salt bind to the cation exchange resin filter, which releases a hydrogen ion ($H^+$) in exchange. The released hydrogen ions react with the dissolved anions from the contaminant salt to form an acid.

In a specific example, the fluid sample 102 may be water, such as sea water or well water, that is contaminated with sodium chloride (NaCl). The ion exchange resin filter 110 is a cation exchange filter that includes hydrogen ions ($H^+$). The hydrogen ions from the ion exchange resin filter 110 exchange with the dissolved sodium ions ($Na^+$) in the fluid sample. The sodium ions bind to the cation exchange resin filter, and the hydrogen ions from the cation exchange filter react with the dissolved chlorine ions ($Cl^-$) in the fluid sample to form hydrochloric acid (HCl). This example reaction is given as follows:

$H_2O+NaCl$ (dissolved)$+$(from cation exchange resin)
$\rightarrow H_2O+HCl+Na^+$(to cation exchange resin)

The presence of acid (for instance, hydrochloric acid) in the effluent 114 that exits the ion conductivity filter 104 increases the cation conductivity of the effluent 114 as compared to an effluent without acid. As the amount of contaminant in the fluid sample 102 increases, the amount of acid in the effluent 114 also increases, causing a corresponding increase in the cation conductivity of the effluent 114. Thus, measuring the cation conductivity of the effluent 114 provides an indication of whether the fluid sample is contaminated with salt. A high cation conductivity value indicates that the fluid sample is contaminated. Conversely, if the fluid sample 102 has little to no salt contamination, the cation conductivity of the effluent 114 will be substantially the same as the cation conductivity of a baseline, uncontaminated sample, such as a sample of pure water.

Figure 2:
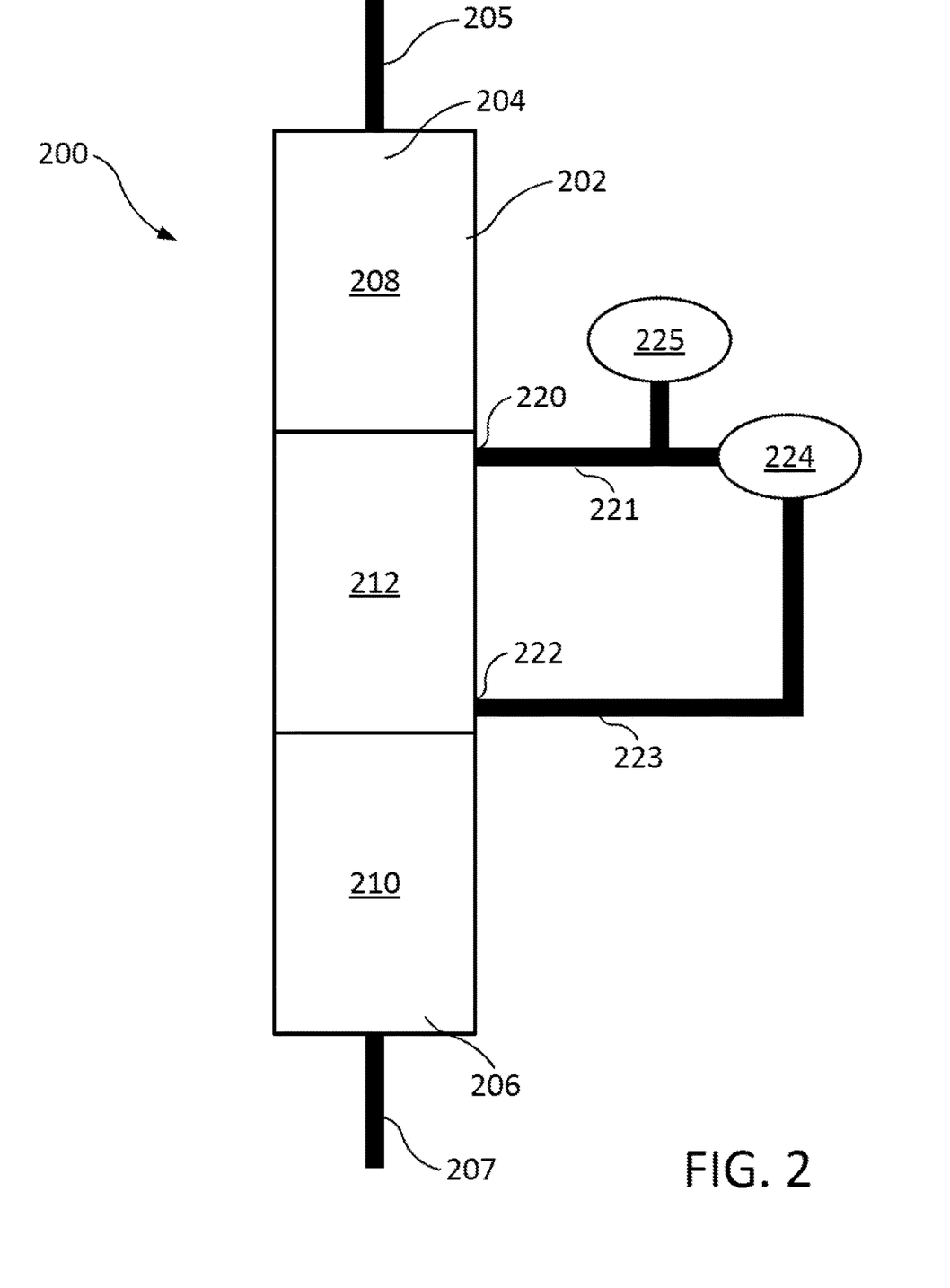
FIG. 2 is a diagram of an electrical conductivity filter.

Referring to FIG. 2, an example laboratory-scale cation conductivity filter 200 includes a filter housing 202 with an inlet 204 at one end of the filter housing 202 and an outlet 206 at the opposite end of the filter housing 202. The inlet 204 and outlet 206 can be connected to tubing 205, 207, respectively, via a screw connection, press fit connection, or other suitable fluid tight connection. The inlet 204 and outlet 206 are fluidically connected to an interior of the filter housing 202 such that fluid entering the filter housing 202 via the inlet 204 can flow through the filter housing 202 and exit the filter housing 202 via the outlet 206. The filter housing 202 can be, for instance, a cylindrical housing. The filter housing 202 is formed of material that is non-reactive to the filters housed in the filter housing and to the fluid samples to be filtered through the cation filter 200. The filter housing has a length of up to about 12 cm, for instance, 10-12 cm. The width of the housing is up to about 2 cm, for instance, 1-2 cm. The thickness of the walls of the housing is up to about 0.4 cm, for instance, 0.2-0.4 cm.

A first cellulose filter 208 is disposed in the interior of the filter housing 202, adjacent to the inlet 204. A second cellulose filter 210 is disposed in the interior of the filter housing 202, adjacent to the outlet 206. A cation exchange resin filter 212 is disposed in the interior of the filter housing 202, between the first and second cellulose filters 208, 210. The filters 208-212 are arranged in the interior of the filter housing 202 such that fluid entering the filter housing 202 via the inlet 204 flows first through the first cellulose filter 208, then through the cation exchange resin filter 212, then through the second cellulose filter 210, before exiting from the filter housing 202 via the outlet 206. The first cellulose filter 208 is designed to capture solids suspended in the fluid that flows into the electrical conductivity filter 200, and can be sized based on the expected size of such solids. For instance, the first cellulose filter 208 can be a 0.45 µm filter. The first cellulose filter has a length of up to about 0.4 cm, for instance, 0.2-0.4 cm, and is dimensioned to fill the width of the interior space of the housing. In some examples, the cellulose filter is made from high-quality cotton linters, such as cotton linters that have been treated to achieve a minimum alpha cellulose content of 98% and certified not to leach ions raising the electrical conductivity to less than about 0.1-0.2 us/cm (micro Siemens per centimeter). In some examples, a glass microfiber or quartz filter is used instead of a cellulose filter.

The cation exchange resin filter 212 acts as a medium for cation exchange with the fluid flowing through the cation conductivity filter 200. The cation exchange resin filter 212 has a high surface area-to-volume ratio to facilitate efficient cation exchange. In an example, the cation resin filter is a macro porous polystyrene cross linked with divinylbenzene with spherical beads and having the following technical properties:

| Functional Group | Sulfonic Acid |
| --- | --- |
| Ionic Form | $Na^+$ form or $H^+$ |
| Total Capacity | 1.8 eq/L (equivalent per liter) (39.3 kg/ft$^3$) (Na+ form) |
| Moisture Retention | 48-53% (Na+ form) |
| Particle Size Range | 300-1200 µm |
| Uniformity Coefficient | 1.7 (maximum) |
| Reversible Swelling, Na+ → H+ | 4% (maximum) |
| Specific Gravity | 1.25 |

The material for the cation exchange resin filter 212 is capable of binding to negatively charged ions in the fluid sample, such as contaminant cations in the fluid sample, such as calcium ions, magnesium ions, sodium ions, ammonium ions, or other cations. In exchange, the cation exchange resin filter 212 releases hydrogen ions into the fluid sample. The cation exchange resin filter 212 can be formed of a material with acidic functional groups, such as carboxylic acid groups, sulfonic acid groups, or other appropriate acidic functional groups, that can supply hydrogen ions to the fluid sample. For instance, the sulfonic acid group is the source of the $H^+$, which gives this chemical structure the ability to behave as a reactive acid.

The second cellulose filter 210 is designed to capture particulate matter from the cation exchange resin filter 212, to prevent particulate matter from leaching into the fluid sample that is output from the cation conductivity filter 200. The second cellulose filter 210 can be sized based on the expected size of such solids. For instance, the second cellulose filter 210 can be a 0.45 µm filter. The materials and design characteristics of the second cellulose filter are similar to those discussed supra for the first cellulose filter.

The dimensions and design characteristics of the cellulose filters and cation exchange filter are selected to allow the exchange to occur with a reasonable time rate that enables a measurable amount of a sample at the outlet.

A side inlet 220 and a side outlet 222 are disposed along the length of the filter housing 202. The side inlet 220 and side outlet 222 are aligned with the cation exchange resin filter 212, with the distance between the side inlet 220 and the inlet 204 of the filter housing 202 being less than the distance between the side outlet 222 and the inlet 204 of the filter housing 202.

The side inlet 220 can be fluidically connected to a fluid reservoir 224 via inlet tubing 221. Fluid from the fluid reservoir 224 can enter the cation conductivity filter 200 via the side inlet 220, flow along at least a portion of the length of the cation exchange resin filter 212, and exit the cation conductivity filter 200 via the side outlet 222. In some examples, the fluid from the side outlet 222 returns to the fluid reservoir 224 via outlet tubing 223. In some examples, the fluid from the side outlet 222 is discarded. The fluid reservoir 224 can be a reservoir of a cleaning fluid, such as water, that can be flowed along the cation exchange resin filter 212 to rinse the cation exchange resin filter 212 prior to use. The fluid reservoir 224 can be a reservoir of a regeneration fluid, such as an acid (for instance, 5% hydrochloric acid or 5% sulfuric acid), that can be flowed along the cation exchange resin filter 212 for cation regeneration. In some examples, the side inlet 220 is configured to be connected to multiple reservoirs, such as to both a cleaning fluid reservoir 225 and a regeneration fluid reservoir 224.

Effluent exiting the cation conductivity filter 200 via the outlet 206 flows to a cation conductivity sensor (not shown), where the cation conductivity of the effluent is measured.

Figure 3:
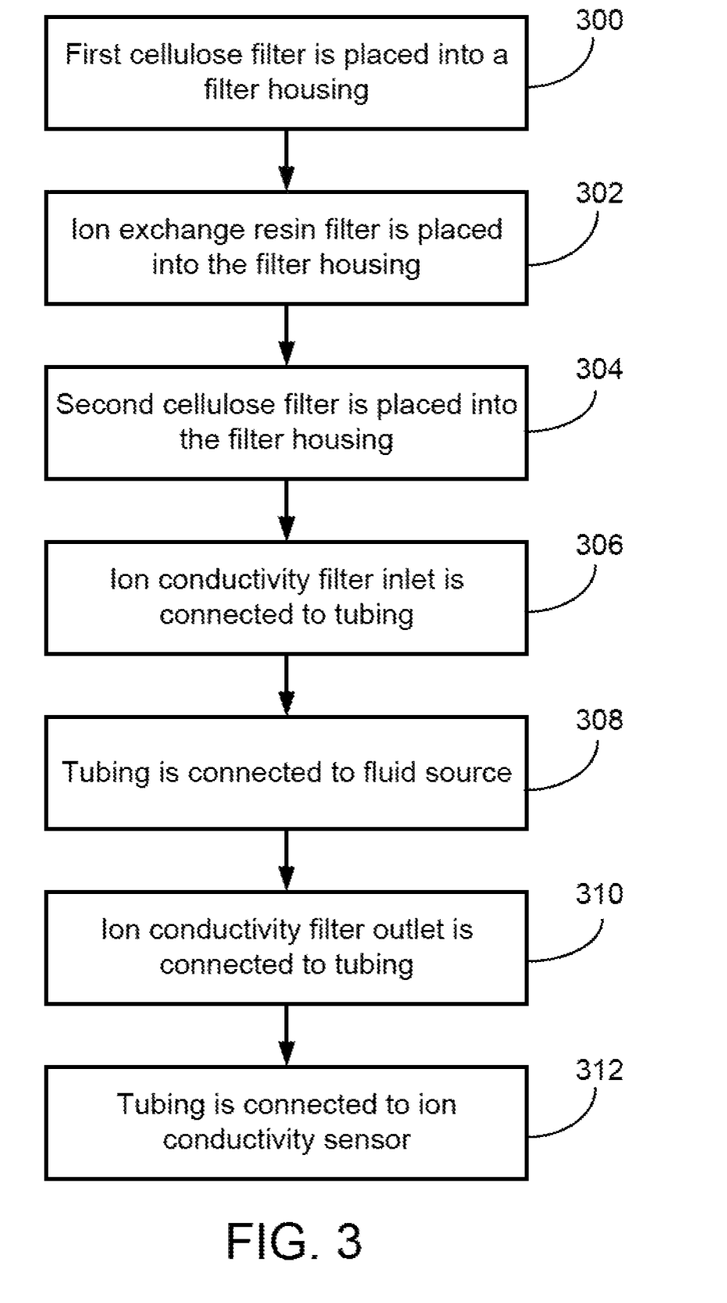
FIGS. 3 and 4 are flow charts.

Referring to FIG. 3, in an example process for making a laboratory-scale ion conductivity measurement system, a first cellulose filter is placed into the interior of a filter housing adjacent to an inlet of the ion conductivity filter (300). An ion exchange resin filter (for instance, a cation exchange resin filter) is placed into the interior of the filter housing adjacent to the first cellulose filter (302). A second cellulose filter is placed into the interior of the filter housing adjacent to the first cellulose filter and to an outlet of the ion conductivity filter (304). In some examples, the first cellulose filter can be placed adjacent to the outlet of the filter housing and the second cellulose filter can be placed adjacent to the inlet of the filter housing.

The inlet of the ion conductivity filter is connected to tubing, for instance, by a screw connection, press fit connection, or other suitable fluid tight connection (306). The tubing is fluidically connected to a fluid source such that a fluid sample can be provided to the inlet of the electrical conductivity filter via the tubing (308). In some examples, rather than connecting the tubing to a fluid source, a fluid sample is provided directly to the tubing, for instance, by a laboratory technician.

The outlet of the ion conductivity filter is connected to tubing, for instance, by a screw connection, press fit connection, or other suitable fluid tight connection (310). The tubing is fluidically connected to an ion conductivity sensor that can measure the ion conductivity of the effluent leaving the ion conductivity filter (312). In some examples, the ion conductivity sensor can be connected close to the outlet of the filter housing to reduce the likelihood of gas bubbles being present in the ion conductivity sensor.

Figure 4:
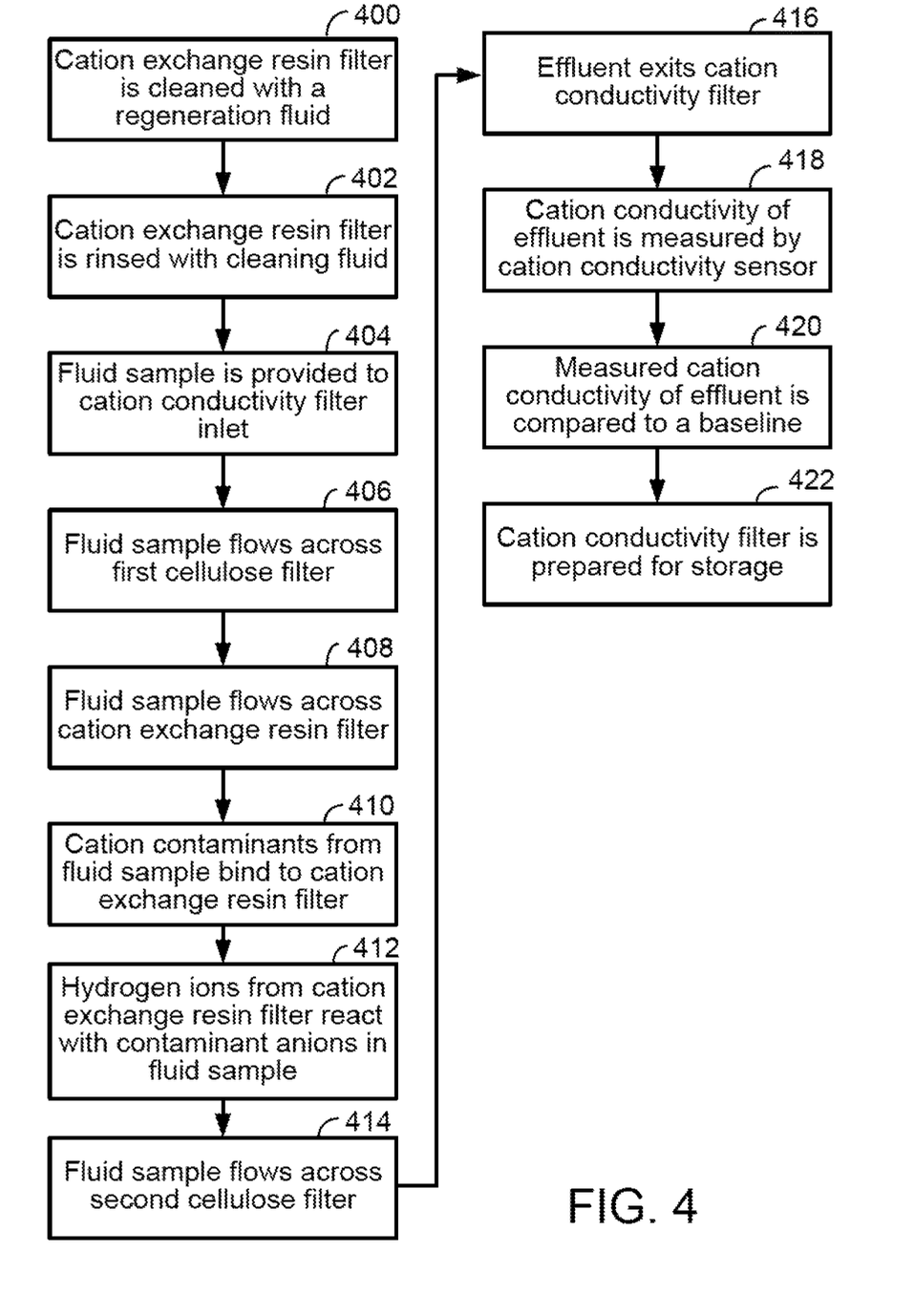

Referring to FIG. 4, in an example process for operating a laboratory-scale cation conductivity measurement system, a cation exchange resin filter disposed in a filter housing of a cation conductivity filter is cleaned with a regeneration fluid to regenerate the resin (400). For instance, the resin is regenerated by flowing an acidic regeneration fluid, such as a solution of 5% hydrochloric acid or 5% sulfuric acid in water, is flowed across the cation exchange resin filter. The regeneration solution is input into a side inlet of the cation conductivity filter, flows along the length of the cation exchange resin filter, and exits from the electrical conductivity filter via a side outlet. The cation exchange resin filter is rinsed with a cleaning fluid, such as water, that is input into the side inlet of the cation conductivity filter and exits from the cation conductivity filter via the side outlet (402).

A fluid sample is provided to the inlet of the cation conductivity filter (404). The fluid sample first flows across a first cellulose filter disposed in a housing of the cation conductivity filter (406). The first cellulose filter captures solids that are suspended in the fluid sample. The fluid sample then flows across a cation exchange resin filter disposed in the housing of the cation conductivity filter (408). Cation exchange occurs between the cation exchange resin filter and cations of any salt contaminant that may be in the fluid sample, with cations from the salt contaminant (such as sodium ions) binding to the cation exchange resin filter and hydrogen ions from the cation exchange resin filter entering into solution in the fluid sample (410). The hydrogen ions from the cation exchange resin filter react with anions from the salt contaminant (such as chlorine ions) to produce an acid (such as hydrochloric acid) (412).

The fluid sample, having undergone cation exchange, then flows across a second cellulose filter disposed in the housing of the cation conductivity filter (414). The second cellulose filter captures particulate matter from the cation exchange resin filter. The fluid sample exits the cation conductivity filter as an effluent (416) and the cation conductivity of the effluent is measured by the cation conductivity sensor (418). The measured cation conductivity is compared to a baseline electrical cation conductivity, such as the electrical cation conductivity of pure water (420). If the measured cation conductivity is greater than the baseline cation conductivity by at least a threshold amount, the fluid sample can be considered to be contaminated with a salt. If the measured cation conductivity is within the threshold amount of the baseline cation conductivity, the fluid sample can be considered to be substantially uncontaminated.

After use, the cation conductivity filter can be rinsed, detached from the various tubings, filled with a fluid, such as demineralized water, and capped at the inlet and outlet, for instance, for storage or transport (422).

In some examples, the contamination of the fluid sample can be evaluated based on a threshold difference between the cation conductivity of the effluent and a baseline cation conductivity, such as the cation conductivity of pure water. If the measured cation conductivity of the effluent is greater than the baseline cation conductivity by at least a threshold amount, the fluid sample can be considered as contaminated with salt. If the measured cation conductivity of the effluent is within the threshold amount of the baseline cation conductivity, the fluid sample can be considered to be substantially uncontaminated. The threshold can be, for instance, 0.5 μmho per centimeter, with higher measured cation conductivity values indicating greater contamination of the tested sample]

EXAMPLE

A laboratory scale cation conductivity measurement system including a cation conductivity filter such as that shown in FIG. 2 was tested to measure the cation conductivity of two different fluid samples with compositions as shown in the following Table. As indicated in the Table, the conductivity of the two samples was different, indicating a different level of contamination in each sample.

| Sample | Cation column Inlet Sample Analysis Electrical Conductivity at 25° C. umhos/cm | Cation column Outlet Sample Analysis Electrical Cation Conductivity at 25° C. umhos/cm |
| --- | --- | --- |
| 1 | 6.0 | 1.2* |
| 2 | 6.0 | 0.4 |

*The conductivity result shows a higher electrical cation conductivity for sample 1 indicating a possible contamination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. An apparatus for measuring cation conductivity of a fluid sample, the apparatus comprising:
   a housing having an inlet disposed at a first end of the housing and an outlet disposed at a second end of the housing, the second end opposite the first end, wherein the inlet of the housing is configured to receive the fluid sample;
   a first cellulose filter disposed in the housing adjacent to the inlet;
   a second cellulose filter disposed in the housing adjacent to the outlet;
   a cation exchange resin filter disposed in the housing between the first cellulose filter and the second cellulose filter;
   a side inlet disposed along a length of the housing between a position of the first cellulose filter and a position of the second cellulose filter, the side inlet fluidically connected to a reservoir of regeneration fluid and configured to be connected to an additional reservoir of cleaning fluid;
   a side outlet disposed along the length of the housing between the position of the first cellulose filter and the position of the second cellulose filter, the side outlet fluidically connected to the reservoir of regeneration fluid,
   wherein the outlet of the housing is configured to be fluidically connected to a cation conductivity sensor configured to measure a cation conductivity of an effluent output from the outlet of the housing,
   wherein the first and second cellulose filters comprise cotton linters that have been treated to achieve a minimum alpha cellulose content of 98%, and
   wherein the cation exchange resin filter comprises a macro porous polystyrene cross linked with divinylbenzene with spherical beads.

2. The apparatus of claim 1, wherein the first cellulose filter comprises a 0.45 pm cellulose filter.

3. The apparatus of claim 1, wherein the second cellulose filter comprises a 0.45 pm cellulose filter.

4. The apparatus of claim 1, wherein the cation exchange resin filter is formed of a material comprising acidic functional groups.

5. The apparatus of claim 1, wherein the side inlet and the side outlet are aligned with the cation exchange resin filter.

6. The apparatus of claim 1, wherein the reservoir of regeneration fluid comprises a source of hydrochloric acid or sulfuric acid.

7. The apparatus of claim 1, wherein a distance between the side inlet and the inlet of the housing is less than a distance between the side outlet and the inlet of the housing.

8. The apparatus of claim 1, further comprising the cation conductivity sensor.

9. The apparatus of claim 1, further comprising the reservoir of cleaning fluid, wherein the reservoir of cleaning fluid is fluidically connected to the side inlet.

10. The apparatus of claim 9, wherein the side outlet is fluidically connected to the reservoir of cleaning fluid.

\* \* \* \* \*

UNITED STATES PATENT AND TRADEMARK OFFICE
CERTIFICATE OF CORRECTION

| | |
|---|---|
| PATENT NO. | : 12,061,182 B2 |
| APPLICATION NO. | : 16/942589 |
| DATED | : August 13, 2024 |
| INVENTOR(S) | : Ali M. Al-Tawfiq and Ali M. Al-Sulaiman |

It is certified that error appears in the above-identified patent and that said Letters Patent is hereby corrected as shown below:

In the Claims

Column 8, Line 60, Claim 2, please replace "0.45 pm" with -- 0.45 µm --.

Column 8, Line 62, Claim 3, please replace "0.45 pm" with -- 0.45 µm --.

Signed and Sealed this
First Day of October, 2024

Katherine Kelly Vidal
*Director of the United States Patent and Trademark Office*